United States Patent [19]

Evans et al.

[11] Patent Number: 4,812,459

[45] Date of Patent: Mar. 14, 1989

[54] ANTI-HYPERTENSIVE PYRANOPYRIDINE COMPOUNDS

[75] Inventors: John M. Evans, Roydon; Geoffrey Stemp; Frederick Cassidy, both of Harlow, all of England

[73] Assignee: Beecham Group p.l.c., England

[21] Appl. No.: 871,711

[22] Filed: Jun. 6, 1986

[30] Foreign Application Priority Data

Jun. 8, 1985 [GB] United Kingdom ............... 8514538
Nov. 9, 1985 [GB] United Kingdom ............... 8527713

[51] Int. Cl.$^4$ .............. A61K 31/495; A61K 31/40; C07D 491/02
[52] U.S. Cl. .............................. 514/254; 514/241; 514/252; 514/253; 514/269; 514/274; 514/302; 544/216; 544/238; 544/284; 544/295; 544/296; 544/333; 544/362; 544/363; 544/405; 546/15; 546/115; 546/116; 546/122; 546/230; 546/231
[58] Field of Search .............. 544/333, 405, 362, 363, 544/216, 284, 295, 296, 238; 546/115, 116, 122, 15, 230, 231; 514/254, 302, 241, 252, 253, 274, 269

[56] References Cited

U.S. PATENT DOCUMENTS 4,496,565 1/1985 Evans et al. .................. 514/222
4,616,021 10/1986 Ashwood et al. ............. 546/141

FOREIGN PATENT DOCUMENTS 95316 11/1983 European Pat. Off. .

OTHER PUBLICATIONS

Evans et al., CA 101-72609g.
Evans, CA 100-174665u.
Faruk, CA 100-120887z.
Evans et al, CA 99-88053x.
Evans et al., CA 102-131914y.
Evans et al., CA 102-113296u, 113297v.

Primary Examiner—Donald G. Daus
Assistant Examiner—Cecilia Shen
Attorney, Agent, or Firm—Jacobs & Jacobs

[57] ABSTRACT

A compound of formula (I) or a pharmaceutically acceptable salt thereof:

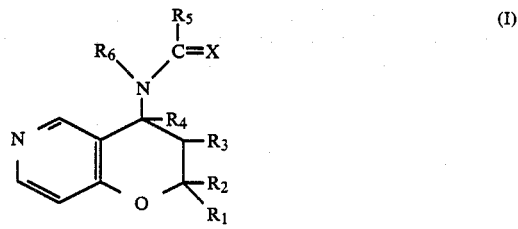

wherein all the symbols are defined in the specification; having pharmacological activity, including blood pressure lowering activity, a process and intermediates for their preparation and their use as pharmaceuticals.

9 Claims, No Drawings

ANTI-HYPERTENSIVE PYRANOPYRIDINE COMPOUNDS

The present invention relates to novel pyranopyridines having pharmacological activity, to a process and intermediates for preparing them, to pharmaceutical compositions containing them, and to their use in the treatment of mammals.

European Patent Publication Nos. 76075, 91748, 93535, 95316, 107423, 120426, 120427, 126311 and 126367 disclose classes of compounds that are described as having blood pressure lowering activity or anti-hypertensive activity.

A structurally distinct class of compounds has now been discovered which are pyranopyridines substituted in the 4-position by a cyclic or acyclic amide, the nitrogen atom of the amide moiety being bonded directly to the carbon atom in the 4-position. Such pyranopyridines have been found to have blood pressure lowering activity, useful in the treatment of hypertension. In addition, these compounds are believed to be K+ channel activators which indicates that they are of potential use in the treatment of disorders associated with smooth muscle contraction of the gastro-intestinal tract, respiratory system, uterus or urinary tract. Such disorders include peptic ulcers, irritable bowel syndrome and diverticular disease, reversible airways obstruction and asthma; premature labour; and incontinence. They are also indicated as of potential use in the treatment of cardiovascular disorders other than hypertension, such as congestive heart failure, angina, peripheral vascular disease and cerebral vascular disease.

Accordingly, the present invention provides a compound of formula (I) or a pharmaceutically acceptable salt thereof:

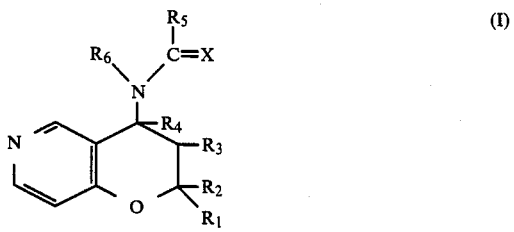

wherein:

one of $R_1$ and $R_2$ is hydrogen or $C_{1-4}$ alkyl and the other is $C_{1-4}$ alkyl or $R_1$ and $R_2$ together are $C_{2-5}$ polymethylene;

either $R_3$ is hydrogen, hydroxy, $C_{1-6}$ alkoxy or $C_{1-7}$ acyloxy and $R_4$ is hydrogen or $R_3$ and $R_4$ together are a bond;

$R_5$ is hydrogen; $C_{1-6}$ alkyl optionally substituted by up to three halo atoms, by hydroxy, $C_{1-6}$ alkoxy, $C_{1-6}$ alkoxycarbonyl, carboxy or amino optionally substituted by one or two independent $C_{1-6}$ alkyl groups or disubstituted by $C_{4-5}$ polymethylene; $C_{2-6}$ alkenyl; amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen; or aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups; or (when X is O), $R_5$ is selected from the class of carboxy, $C_{1-6}$ alkoxycarbonyl, or aminocarbonyl optionally substituted by one or two $C_{1-6}$ alkyl groups; and $R_6$ is hydrogen or $C_{1-6}$ alkyl; or $R_5$ and $R_6$ together are —$CH_2$—$(CH_2)_n$—Z—$(CH_2)_m$— wherein m and n are 0 to 2 such that m+n is 1 or 2 and Z is $CH_2$, O, S or NR wherein R is hydrogen, $C_{1-9}$ alkyl, $C_{2-7}$ alkanoyl, phenyl $C_{1-4}$-alkyl, naphthylcarbonyl, phenylcarbonyl or benzyl-carbonyl optionally substituted in the phenyl or naphthyl ring by one or two of $C_{1-6}$ alkyl, $C_{1-6}$ alkoxy or halogen; or R is heteroarylcarbonyl;

X is oxygen or sulphur; or $R_5$, $R_6$, X and N together are tetrahydroisoquinolinone or tetrahydroisoquinolin-thione optionally substituted in the phenyl ring as defined for R above;

the nitrogen-containing group in the 4-position being trans to the $R_3$ group when $R_3$ is hydroxy, $C_{1-6}$ alkoxy or $C_{1-7}$ acyloxy.

Preferably, $R_1$ and $R_2$ are both $C_{1-4}$ alkyl, in particular both methyl.

When $R_3$ is $C_{1-6}$ alkoxy and $R_4$ is hydrogen, preferred examples of $R_3$ include methoxy and ethoxy, of which methoxy is more preferred. When $R_3$ is $C_{1-7}$ acyloxy and $R_4$ is hydrogen, a preferred class of $R_3$ is unsubstituted carboxylic acyloxy, such as unsubstituted aliphatic acyloxy. However, it is more preferred that $R_3$ and $R_4$ together are a bond, or that $R_3$ and $R_4$ are both hydrogen, or, in particular, that $R_3$ is hydroxy and $R_4$ is hydrogen.

Examples of $R_5$, when $C_{1-6}$ alkyl, include methyl, ethyl and n- and iso-propyl. Preferably such $R_5$ is methyl.

A sub-group of $R_5$, when $C_{1-6}$ alkyl halogen is $C_{1-6}$ alkyl substituted by fluoro, chloro or bromo. Examples thereof include methyl or ethyl terminally substituted by one, two or three fluoro, chloro or bromo.

Examples of $R_5$, when $C_{1-6}$ alkyl substituted by hydroxy, include methyl or ethyl terminally substituted by hydroxy.

A sub-group of $R_5$, when $C_{1-6}$ alkyl substituted by $C_{1-6}$ alkoxy is $C_{1-6}$ alkyl substituted by methoxy or ethoxy. Examples thereof include methyl or ethyl terminally substituted by methoxy or ethoxy.

A sub-group of $R_5$, when $C_{1-6}$ alkyl substituted by $C_{1-6}$ alkoxycarbonyl is $C_{1-6}$ alkyl substituted by methoxycarbonyl or ethoxycarbonyl. Examples thereof include methyl or ethyl terminally substituted by methoxycarbonyl or ethoxycarbonyl.

Examples of $R_5$, when $C_{1-6}$ alkyl substituted by carboxy include methyl or ethyl terminally substituted by carboxy.

Examples of $R_5$ when alkyl substituted by amino optionally substituted by one or two independent $C_{1-6}$ alkyl groups include a group $(CH_2)_nNR_9R_{10}$ where n is 1 to 6, and $R_9$ and $R_{10}$ are each independently hydrogen or $C_{1-6}$ alkyl or together are $C_4$ or $C_5$ polymethylene. Examples of n include 1 and 2, in particular 1. Preferably $R_9$ and $R_{10}$ are each independently selected from hydrogen and methyl.

Examples of $R_5$, when $C_{2-6}$ alkenyl include vinyl, prop-1-enyl, prop-2-enyl, 1-methylvinyl, but-1-enyl, but-2-enyl, but-3-enyl, 1-methylenepropyl, or 1-methyl-prop-2-enyl, in both their E and Z forms where stereoisomerism exists.

Examples of $R_5$ when amino optionally substituted as hereinbefore defined include an amino optionally substituted by a methyl, ethyl, propyl, butyl, allyl or trichloroacetyl group or by a phenyl group optionally substituted by one methyl, methoxy or chloro group or atom, in particular amino, methylamino, and phenylamino optionally substituted in the phenyl ring by one methyl, methoxy or chloro group or atom.

Examples of $R_5$ when aryl include phenyl and naphthyl, of which phenyl is preferred.

A sub-group of $R_5$ heteroaryl or heteroaryl for an R moiety in Z, is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from.the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl.

Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Preferably, the number of groups or atoms for optional substitution of aryl or heteroaryl is one, two, three or four.

Preferred examples of the groups or atoms for optional substiution of aryl or heteroaryl include methyl, methoxy, hydroxy, chloro, fluoro, nitro or cyano, most preferably fluoro.

A sub-group of $R_5$ is phenyl or naphthyl or a 5- or 6-membered monocyclic or a 9- or 10-membered bicyclic heteroaryl, the phenyl, naphthyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

A preferred subgroup of phenyl optionally substituted as hereinbefore defined is phenyl, 4-substituted phenyl, 3-substituted phenyl, 2-substituted phenyl, 2,4, 2,6 and 3,4-disubstituted phenyl and 3,4,5-trisubstituted phenyl.

A preferred sub-group of 5- or 6-membered monocyclic or 9- or 10-membered bicyclic heteroaryl optionally substituted as hereinbefore defined is unsubstituted or mono-substituted 5- or 6-membered monocyclic or 9- or 10-membered bicyclic heteroaryl, in particular unsubstituted 5- or 6-membered monocyclic or 9- or 10-membered bicyclic heteroaryl.

When X is 0, examples of $R_5$ also include carboxyl, methoxycarbonyl, ethoxycarbonyl, aminocarbonyl, methylamino-carbonyl and dimethylaminocarbonyl.

$R_5$ and $R_6$, when together are $-CH_2-(CH_2)_n-Z-(CH_2)_m-$ as defined the resulting radical substituting the pyranopyridine in the 4-position is preferably either pyrrolidonyl or piperidonyl. Other examples of 4-substituents when $R_5$ and $R_6$ are joined together include those described in U.S. Pat. No. 4,496,656.

When Z is other than $CH_2$, m is often 0 or 1 and n is often 0 or 1. Suitable examples of R when Z is NR include hydrogen, methyl ethyl, n- and iso-propyl, n-, sec- and tert- butyl, benzyl, phenylcarbonyl or benzylcarbonyl optionally substituted in the phenyl ring by methyl, methoxy, chloro or bromo; furylcarbonyl, thienylcarbonyl, pyrrolylcarbonyl or indolylcarbonyl. Preferably R is hydrogen, methyl, n-butyl, acetyl, benzyl, benzylcarbonyl, phenylcarbonyl or furylcarbonyl. Most preferably R is hydrogen.

Preferred examples of $R_5$ and $R_6$ are $R_5$ is methyl or halophenyl, such as 2- or 4-fluorophenyl and $R_6$ hydrogen and $R_5$ and $R_6$ together are $C_3$ or $C_4$ polymethylene.

Preferably, X is oxygen.

Examples of a pharmaceutically acceptable salt of a compound of formula (I), when the compound contains a salifiable substituent which is an optionally substituted amino group, include acid addition salts such as the hydrochloride and hydrobromide salts. Such a salifiable group may be within an $R_5$ group. A carboxy group within $R_5$ may also be salified to form metal salts, such as alkali metal salts, or optionally substituted ammonium salts.

It will also be appreciated that the pyridine in the compound of formula (I) is also salifiable, to give pyridine salts with acids, such as those with HCl and HBr. Alternatively, internal salts such as the N-Oxide may be formed by per-acid oxidation of the corresponding compound of formula (I).

The compounds of formula (I) may also exist as solvates such as hydrates and the invention extends to these; such solvates are included wherever a compound of formula (I) is herein referred to.

The compounds of formula (I), wherein $R_3$ is hydrogen, hydroxy, $C_{1-6}$ alkoxy or $C_{1-7}$ acyloxy and $R_4$ is hydrogen, are asymmetric, and, therefore, can exist in the form of optical isomers.

The present invention extends to all such isomers individually and as mixtures, such as racemates.

Examples of compounds of formula (I) include the compounds prepared in the Examples hereinafter.

The present invention also provides a process for the preparation of a compound of formula (I) or a pharmaceutically acceptable salt thereof, which comprises;
(i) acylating a compound of formula (II):

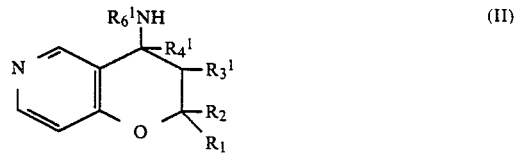

(II)

wherein, $R_1$ and $R_2$ are as hereinbefore defined, $R_3^1$ is hydroxy, $C_{1-6}$ alkoxy or $C_{1-7}$ acyloxy, and $R_6^1$ is hydrogen or $C_{1-6}$ alkyl, the $R_6^1NH$ group being trans to the $R_3^1$ group, (a) with an acylating agent of formula (III):

$R_8-CO-L_1$ (III)

wherein $L_1$ is a leaving group, and $R_8$ is hydrogen, $C_{1-6}$ alkoxycarbonyl, $C_{1-6}$ alkyl optionally substituted by halogen, hydroxy, $C_{1-6}$ alkoxy, $C_{1-6}$ alkoxycarbonyl, carboxy or amino optionally substituted as hereinbefore defined for $R_5$, $C_{2-6}$ alkenyl or optionally substituted aryl or heteroaryl as hereinbefore defined for $R_5$, or a group convertible to $R_5$ as hereinbefore defined, and thereafter, when $R_6$ is hydrogen and $R_8$ is $Y(CH_2)_z$, where z is 3 or 4 and Y is a leaving group, cyclising the resultant compound;

(b) with a compound of formula (IV)

$$X=C=N-R_{11} \qquad (IV)$$

wherein $R_{11}$ is hydrogen, $C_{1-6}$ alkyl, $C_{1-6}$ alkenyl, $C_{1-6}$ alkanoyl optionally substituted by up to three halo atoms, or phenyl optionally substituted by $C_{1-6}$ alkyl, $C_{1-6}$ alkoxy or halogen; and X is oxygen or sulphur, and thereafter when $R_{11}$ is hydrogen, optionally converting $R_{11}$; or (ii) where, in the resultant compound of formula (I), $R_5$ and $R_6$ are joined together or $R_5$ is aminocarbonyl, reacting a compound of formula (V):

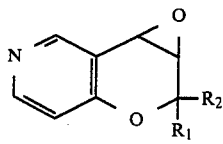

wherein $R_1$ and $R_2$ are as hereinbefore defined, with a compound of formula (VI):

$$R_{13}NHCOR_{12} \qquad (VI)$$

wherein $R_{13}$ is $R_6$ as defined and $R_{12}$ is aminocarbonyl; $R_{12}$ and $R_{13}$ together are $-CH_2-(CH_2)_n-Z-(CH_2)_m-$ or $R_{12}NHCOR_{12}$ is tetrahydroisoquinolinone; optionally converting $R_3$ in the resulting compound into another $R_3$; in the case where $R_3$ and $R_4$ in the resulting compound are hydroxy and hydrogen respectively, optionally dehydrating the compound to give another compound wherein $R_3$ and $R_4$ together are a bond, and optionally reducing the resulting compound wherein $R_3$ and $R_4$ together are a bond, to give another compound, wherein $R_3$ and $R_4$ are each hydrogen; and optionally thiating the $R_6-N-CO-R_5$ group in the resulting compound to give a compound wherein X is sulphur; and optionally forming a pharmaceutically acceptable salt thereof.

In the process variant (i) (a) acylation of a compound of formula (II) with an acylating agent of formula (III), the leaving group $L_1$ is a group that is displaceable by a primary or secondary amino nucleophile. Examples of such a group include $C_{1-4}$ alkanoyloxy, and halogen, such as chloro and bromo or hydroxy. When the leaving group $L_1$ is either of these examples, the acylating agent of formula (III) is either an acid anhydride or an acid halide. When it is an acid anhydride, it may be a mixed or simple anhydride. If it is a mixed anhydride, it may be prepared in situ from a carboxylic acid and an acid halide, although this is less preferred than using the halide itself. When $L_1$ is hydroxy, conventional coupling methods using dicyclohexylcarbodiimide are suitable.

In process variant (i) (a), when $R_5$ in the desired compound of formula (I) is an $R_5$ optionally substituted amino-substituted alkyl group as hereinbefore defined, it is preferred that $R_8$ is a group convertible to the $R_5$ substituted alkyl group as hereinbefore defined, in particular that it is $C_{1-6}$ alkyl substituted by halo, especially bromo. The $R_8$ halo substituent in the resultant compound of process variant (i) (a) may be converted to an $R_5$ substituent which is amino optionally substituted as hereinbefore defined by a conventional amination reaction with ammonia or a corresponding alkyl- or dialkylamine. When $R_8$ is $C_{1-6}$alkoxycarbonyl, this may be converted to $R_5$ is carboxy by conventional hydrolysis.

Less favourably $R_8$ may be $C_{1-6}$ alkyl substituted by protected amino, protected $C_{1-6}$ alkylamino or amino substituted by two independent $C_{1-6}$ alkyl groups, it being necessary to protect the $R_8$ amino function in process variant (i) (a).

When the acylating agent of formula (III) is an acid anhydride, the acylation of the compound of formula (II) may be carried out in the presence of an acid acceptor, such as sodium acetate, optionally using the anhydride as the solvent.

When the acylating agent of formula (III) is an acid halide, the acylation of the compound of formula (II) is, preferably, carried out in a non-aqueous medium, such as dichloromethane, in the presence of an acid acceptor, such as triethylamine, trimethylamine, or calcium, potassium or sodium carbonate.

When the acylating agent of formula (III) is an acid the acylation of a compound of formula (II) is conveniently performed in the presence of a dehydrating agent, such as dicyclohexyldicarbodiimide in an inert solvent, such as dimethylformamide at a temperature of 0° C. to ambient.

When $R_3^1$ in a compound of formula (II) is hydroxy, there is a risk of a side-reaction between the hydroxy group and the acylating agent of formula (III). However, the reaction may be carried out under controlled conditions such that only the amine, $R_6^1NH-$ is acylated, for example, by using a $C_{2-9}$ acyloxy group as the leaving group $L_1$, in the acylating agent of formula (III) in the manner as previously described for an acid anhydride, and/or effecting the reaction at relatively low temperature, e.g. at below 10° C. Alternatively $R_3^1$ may be $C_{1-7}$ acyloxy in a compound of formula (II), although less preferably if $R_3$ in the resultant compound of formula (I) is to be hydroxy, and, after reaction with the acylating agent of formula (III), be converted into hydroxy, as described hereinafter.

When $R_8$ is $Y(CH_2)_z$ where the variables are as hereinbefore defined, the leaving group Y is a group that is displaceable by a secondary amino nucleophile adjacent to a carbonyl function. A preferred example is chloro.

The cyclisation reaction when $R_8$ is $Y(CH_2)_z$ where the variables are as hereinbefore defined is preferably carried out in an inert solvent such as dimethylformamide.

In process variant (i) (b), when $R_{11}$ in a compound of formula (IV) is $C_{1-6}$ alkyl, $C_{1-6}$ alkanoyl optionally substituted as hereinbefore defined, or phenyl optionally substituted as hereinbefore defined, the reaction between the compounds of formulae (II) and (IV) is, preferably, carried out in a solvent, such as methylene chloride, at below room temperature, in particular below 10° C. When $R_{11}$ is hydrogen, the reaction between the compounds of formulae (II) and (IV) is, preferably, carried out using a corresponding alkali metal cyanate or thiocyanate, for example that of sodium or potassium, in an optionally methanolic aqueous medium acidified with a mineral acid, such as dilute hydrochloric acid. A slightly elevated temperature such as 50° to 90° C. is apt.

In the process variant (ii) reaction of a compound of formula (V) with a compound of formula (VI), it is particularly preferred that the reaction is carried out under basic conditions so as to facilitate the formation of the anion of the compound of formula (VI), for example, in the presence of sodium hydride.

The reaction of the compounds of formulae (II) with (III) or (IV) results in a compound of formula (I) wherein $R_3$ is hydroxy, $C_{1-6}$ alkoxy or $C_{1-7}$ acyloxy, whereas the reaction of the compounds of formulae (V) and (VI) results in a compound of formula (I) wherein $R_3$ is hydroxy. Examples of an optional conversion of $R_3$ in a compound of formula (I) into another $R_3$ are generally known in the art. For example, when $R_3$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of an acid acceptor. Alternatively, when $R_3$ is $C_{1-7}$ acyloxy or $C_{1-6}$ alkoxy, it may be converted into hydroxy by conventional hydrolysis or dealkylation respectively.

The optional dehydration of the resulting compound of formula (I), wherein $R_3$ and $R_4$ are hydroxy and hydrogen respectively, into another compound of formula (I), wherein $R_3$ and $R_4$ together are a bond, may be carried out under conventional dehydration conditions, for example, by using a dehydrating agent, such as sodium hydride, in an inert solvent, such as dry tetrahydrofuran, at reflux temperature.

The optional reduction of the resulting compound of formula (I), wherein $R_3$ and $R_4$ together are a bond, into another compound of formula (I), wherein $R_3$ and $R_4$ are each hydrogen, may be carried out by hydrogenation using a catalyst of palladium on charcoal.

The optional thiation of the $R_6$—N—CO—$R_5$ group in a compound of formula (I) to give another compound of formula I, wherein X is sulphur, is, preferably, carried out with conventional thiation agents, such as hydrogen sulphide, phosphorous pentasulphide and Lawesson's reagent (p-methoxyphenylthiophosphine sulphide dimer). The use of hydrogen sulphide and phosphorous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride.

The optional formation of a pharmaceutically acceptable salt may be carried out conventionally. It should be appreciated that formation of an N-Oxide by oxidation may affect other substituents and appropriate modification of reaction conditions and/or protection will be taken where necessary.

A compound of formula (II) may be prepared by reacting a compound of formula (V), as defined hereinbefore, with a compound of formula (VII):

$$R_6^1NH_2 \qquad (VII)$$

wherein $R_6^1$ is as defined hereinbefore; and optionally converting $R_3^1$ hydroxyl in the resulting compound of formula (II) into another $R_3^1$.

The reaction is normally carried out in a solvent, such as a $C_{1-4}$ alcohol, in particular methanol, ethanol or propanol at an ambient or an elevated temperature, for example 12 to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_3^1$ in the resulting compound of formula (II) into a $C_{1-6}$ alkoxy or $C_{1-7}$ acyloxy group may be carried out as described hereinbefore in relation to the corresponding conversion of $R_3$ in a compound of formula (I).

A compound of formula (V) may be prepared by reacting a compound of formula (VIII):

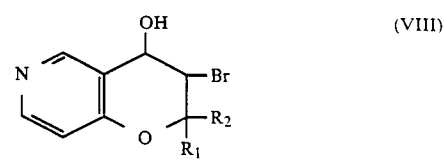

wherein $R_1$ and $R_2$ are as hereinbefore defined, the bromine atom being trans to the hydroxy group, with a base, such as potassium hydroxide, in a solvent, such as ether or aqueous dioxan. It is preferred that the compound of formula (V) is used directly in the reaction with (VI)

A compound of formula (VIII) may be prepared by reacting a compound of formula (IX):

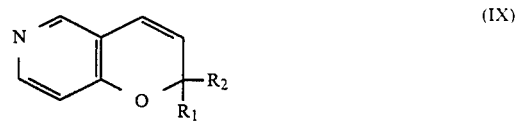

wherein $R_1$ and $R_2$ N-bromosuccinimide in a solvent, such as aqueous dimethyl sulphoxide.

A compound of formula (VIII) may be prepared in accordance with analogous processes to those described in the aforementioned European publications, i.e. by the process depicted below:

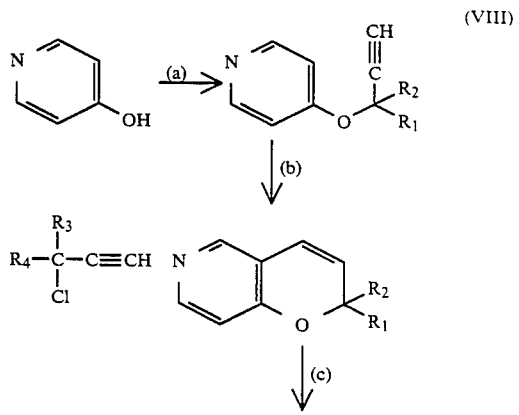

-continued

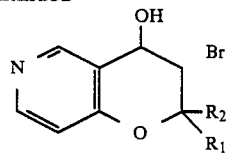

(a) Room temperature; NaOH/40% benzyltrimethylammonium hydroxide in methanol;
(b) Heat in o-dichlorobenzene;
(c) N-bromosuccinimide/dimethylsulphoxide/water;

As mentioned previously, some of the compounds of formula (I) may exist in optically active forms, and the processes of the present invention produce mixtures of such forms. The individual enantiomers may be resolved by conventional methods.

It is preferred that the compounds of formula (I) are isolated in substantially pure, pharmaceutically acceptable form.

The intermediates of formulae (II), (V), (VIII) or (IX) are believed to be novel and represent part of the present invention. The intermediates of formulae (III), (IV), (VI) or (VII) are known and may be prepared in accordance with an appropriate known process.

As mentioned previously, the compounds of formula (I) have been found to have blood-pressure lowering activity. They are therefore useful in the treatment of hypertension. They may also be of potential use in the treatment of other disorders hereinbefore described.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of a spray, aerosol or other conventional method for inhalation, for treating asthma.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

No toxicological effects are indicated at the aforementioned dosage ranges.

The present invention further provides a compound of formula (I) or a pharmaceutically acceptable salt thereof for use in the treatment or prophylaxis of hypertension.

The following descriptions relate to the preparation of intermediates and the following examples relate to the preparation of compounds of formula (I).

All temperatures therein are in ° C.

Description 1

2,2-Dimethyl-2H-pyrano[3,2-c]pyridine

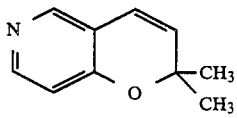
(D1)

p-Hydroxypyridine (32.0 g), 40% benzyltrimethylammonium hydroxide in MeOH (50.7 g) and 3-methyl-3-chlorobut-1-yne (37.4 g) were dissolved in CH$_2$Cl$_2$ (150 mL). To this stirred solution was added NaOH pellets (14.5 g) dissolved in H$_2$O (150 mL) and the resulting mixture stirred vigorously at room temperature for 3.75 days. The layers were separated and the aqueous layer further extracted with CHCl$_3$. The combined organic layers were evaporated and the resulting brown oil was taken up in Et$_2$O and washed with 10% NaOH solution, H$_2$0 and brine before drying over anh. MgSO$_4$. Filtration and evaporation yielded an orange oil (21.0 g) which was boiled in o-dichlorobenzene under N$_2$ for 1 h. Evaporation of the solvent and distillation gave the title pyranopyridine (9.2 g): bp 110° C. /0.18 mmHg; NMR (CDCl$_3$) δ 1.47 (s, 6H)
5.67 (d, J=10, 1H)
6.37 (d, J=10, 1H)
6.67 (d, J=6, 1H)
8.17 (s, 1H)
8.28 (d, J=6, 1H)

Description 2

Trans-3-Bromo-3,4-dihydro-2,2-dimethyl-2H-pyrano[3,2-c]pyridin-4-ol

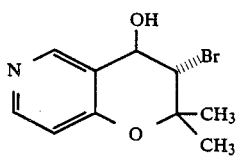
(D2)

To the pyranopyridine (4.0 g) of description 1 dissolved in DMSO (60 mL) and H$_2$O (40 mL) was added NBS (5.3 g) in one portion with vigorous stirring at room temperature. After an additional 9 min of stirring the mixture was poured into H$_2$O (70 mL) containing HCl to pH 2. Extraction with EtOAc, was followed by basification of the aqueous layer to pH 9 with aqueous NaHCO$_3$ and further extraction with EtOAc. Both organic extracts were washed with H$_2$O (pH 7) and brine before drying over anh. MgSO$_4$. The combined extracts were filtered and evaporated and triturated with pentane to give the bromohydrin (2.27 g) as a pale yellow solid. A small portion was recrystallised from EtOAc-pentane: mp 140°–141° C;

NMR (CDCl$_3$) δ 1.46 (s, 3H), 1.65 (s, 3H), 4.14 (d, J=9, 1H), 5.03 (d, J=9, 1H) overlapped by 5.08 (s, 1H exchangeable with D$_2$O), 6.77 (d, J=6, 1H), 8.35 (d, J=6, 1H), 8.62 (s, 1H).

EXAMPLE 1

Trans-3,4-Dihydro-2,2-dimethyl-4-(2-oxopyrrolidin-1-yl) 2H-pyrano[3,2-c]pyridin-3-ol

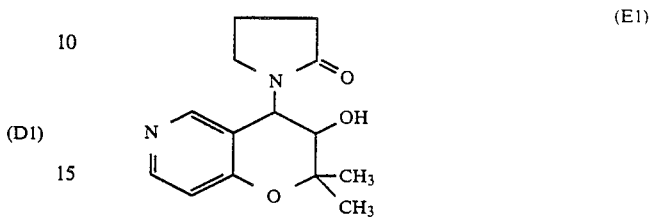
(E1)

The bromohydrin of description 2 (1.2 g) and KOH pellets (1.2 g) were stirred in Et$_2$O (200 mL) at room temperature for 20 h. Filtration and evaporation gave a crude epoxide (0.78 g) which was used directly, without purification, in the next stage.

The epoxide (0.43 g) was added to a solution of 2-pyrrolidinone (0.22 mL) in dry DMSO (10 mL) containing 80% NaH (80 mg), and the reaction mixture stirred under N$_2$ for 24 h at room temperature. Water (100 mL) was added cautiously to the reaction mixture and the aqueous layer extracted with EtOAc. The aqueous layer was basified to pH 14 with aqueous KOH and extracted with EtOAc. The organic extract was washed with H$_2$O (at pH 7) and brine and dried over anh. MgSO$_4$. Filtration and evaporation gave a solid (0.22 g) which was chromatographed (chromatotron, 2mm silica gel, gradient elution with CHCl$_3$->20% MeOH/CHCl$_3$) and recrystallised from EtOAc to give the title compound (74 mg): mp 253° C. ; mass spectrum (EI) M$^+$ at m/z 262.1316. Calcd. for C$_{14}$H$_{18}$N$_2$O$_3$; 262.1313.

EXAMPLE 2

Trans-3,4-Dihydro-2,2-dimethyl-4-(2-oxopyrrolidin-1-yl) -2H-pyrano[3,2-c]pyridin-3-ol oxide (E2)

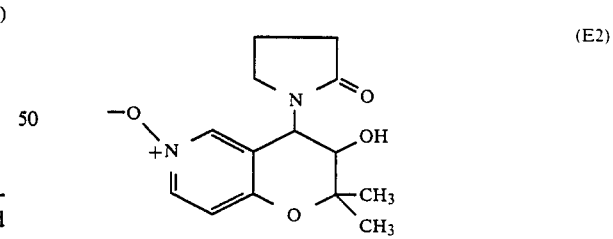
(E2)

The compound of example 1 (102mgm) and m-chloroperbenzoic acid (134mgm) were heated under reflux in chloroform (10 mL) for 2hr. The reaction mixture was cooled and evaporated and the resulting gum was chromatographed (chromatotron; chloroform ->10% methanol-chloroform in a gradient elution), and chromatographically homogenous fractions were combined and recrystallised from ethyl acetate-methanol to give the N-oxide of (E2) as a solid (54mgm) of m.p. 284°–285° C.

Mass spectrum (E.I.) M$^+$ at m/z 278.1255. C$_{14}$H$_{18}$N$_2$O$_4$ requires 278.1243.

EXAMPLE 3

Trans-3,4-Dihydro-2,2-dimethyl-4-(2-oxopiperidin-1-yl)-H-pyrano[3,2-c]pyridin-3-ol (E3)

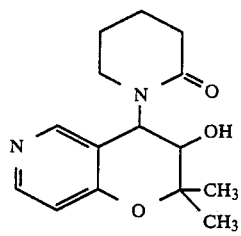

The bromohydrin of description 2 was treated in a similar manner to that described in example 1, and the crude epoxide used directly as follows.

The epoxide (0.95g) in dimethyl sulphoxide (15 mL) was added to a solution of δ-valerolactam (0.64 g) and 80% NaH (0.18 g) in dimethyl sulphoxide (10 mL) and the mixture stirred for 18 hours under nitrogen. Water was added cautiously to the reaction mixture and the pH adjusted to 12 with sodium hydroxide, and the solution saturated with sodium chloride. Extraction with ethyl acetate, gave a crude product which was chromatographed (chromatotron; chloroform −>25% methanol-chloroform in a gradent elution) to give the required product (0.03 g) as a solid. Further extraction of the aqueous layer with chloroform, and distillation of the co-extracted dimethyl sulphoxide gave more crude product which was chromatographed as above to give a further batch of the required material (0.355 g). Solids were combined and recrystallised from ethyl acetate to give the compound of example 3 as colourless crystals (0.232 g); m.p. 241°–243° C. IR (KBr disc): 3500–3100; 1610 cm$^{-1}$.

EXAMPLE 4

Trans-4-Acetylamino-3,4-dihydro-2,2-dimethyl-2H-pyrano-[3,2-c]pyridin-3-ol (E4)

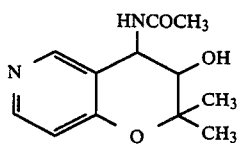

Crude epoxide (1.48 g, prepared as described in example (1) was treated with 0.88 ammonia solution (15 mL) in ethanol (30 mL) during 31 hours. Evaporation gave a crude aminoalcohol (1.56 g) as a foam.

A portion of this aminoalcohol (0.71 g), triethylamine (0.51 mL) and dichloromethane (25 mL) were stirred at 0° C. Acetyl chloride (0.26 mL) was added to this solution, and the mixture stirred for a further 1 hour. The organic layer was washed with water. The aqueous extract was made basic with sodium carbonate and saturated with sodium chloride and extracted with chloroform. The organic layer was dried, filtered and evaporated to leave a solid (0.48 g) which was recrystallised from ethyl acetate to furnish the compound of example 4 as a white solid (0.274 g) of m.p. 208°–210° C.

NMR (CDCl$_3$) δ
1.28 (s, 3H)
1.49 (s, 3H)
2.08 (s, 3H)
3.62 (d, J=10 Hz, 1H)
5.03 (d, J=10 Hz, 1H)
6.79 (d, J=6 Hz, 1H)
8.18 (m, 2H)

EXAMPLE 5

Trans-4-(4-fluorobenzoylamino)-3,4-dihydro-2,2-dimethyl -2H-pyrano[3,2-c]pyridin-3-ol (E5)

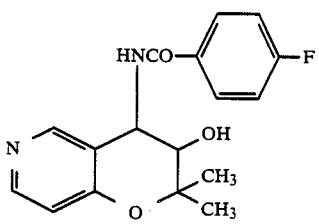

Crude aminoalcohol (0.85 g, prepared as described in example 4) was treated in an identical manner to that described in example 4, with p-fluorobenzoyl chloride.

Chromatography of the crude product (0.654 g) using a gradient elution technique (chromatotron; chloroform methanol) gave the required material which was recrystallised from ethyl acetate-methanol as a crystalline white solid (64 mg) of m.p. 254°–255° C.

Anal. Found: C, 64.29; H, 5.35; N, 8.77;
C$_{17}$H$_{17}$N$_2$O$_3$F req: C, 64.55; H, 5.42; N, 8.86.

EXAMPLE 6

2,2-Dimethyl-4-(2-oxopiperidin-1-yl)-2H-pyrano[3,2-c]pyridine (E6)

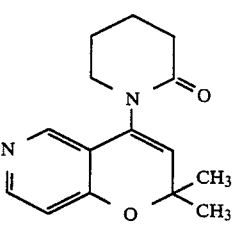

The compound of example 3 (0.40 g) and 80% NaH (0.088 g) were heated under reflux in dry xylene (35 mL) under nitrogen for 2.5 h. A few drops of water were added cautiously and the solution evaporated to give a yellow gum (0.60 g) which was chromatographed (chromototron; chloroform −>25% MeOH-chloroform in a gradient elution) to give a crude product (0.147 g) which was recrystallised from ethyl acetate-pentane to give the title compound (0.086 g) as colourless crystals mp 108°–113° C. .

NMR CDCl$_3$ δ
1.52 (s, 6H)
1.94 (brs, 4H)
2.56 (brs, 2H)
3.49 (m, 2H)
5.59 (s, 1H)
6.72 (d, J=5.5 Hz, 1H)
8.05 (s, 1H)
8.26 (d, J=5.5 Hz, 1H)

EXAMPLE 7

Trans-3,4-dihydro-2,2-dimethyl-4-(2-oxopiperidin-1-yl)-2H-pyrano[3,2-c]pyridin-3-ol oxide (E7)

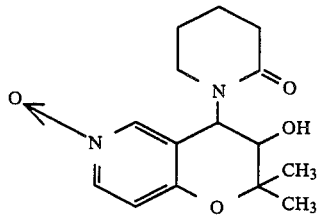
(E7)

The compound of example 3 was treated with m-chloro-acid as described in the preparation of the oxide of example 2, to give the N-oxide (E7) as a solid of m.p. 290°–291° C. from ethyl acetate-methanol.

EXAMPLE 8

Trans-4-(2-fluorobenzoylamino)-3,4-dihydro-2,2-dimethyl -2H-pyrano[3,2-c]pyridin-3-ol (E8)

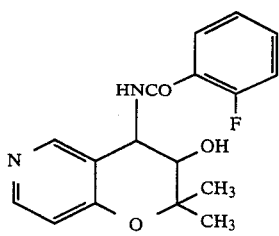
(E8)

The crude aminoalcohol (0.97 g, prepared as described in example 4) was added to a solution of dicyclohexyl-carbodiimide (1.027 g), hydroxybenzotriazole (0.657 g) and 2-fluorobenzoic acid (0.7 g) in dry dimethylformamide (20 mL) at 0° C. The reaction mixture was allowed to attain room temperature, and was stirred for 3 days. The mixture was filtered and evaporated, and the residue chromatographed on silica gel. Elution with 10% methanol-chloroform mixture and recrystallisation from ethyl acetate-methanol furnished the product of example 8 (345 mg) of m.p. 254° C.

NMR (CD$_3$OD) δ 1.33 (s, 3H)

1.53 (s, 3H)

3.81 (d, J=9 Hz, 1H)

5.27 (d, J=9 Hz, 1H)

6.83 (d, J=6 Hz, 1H)

7.10–7.93 (series of m, 4H).

8.23 (d, J=6 Hz, 1h)

8.36 (s, 1h)

EXAMPLE 9

Trans-4-(3-fluorobenzoylamino)-3,4-dihydro-2,2-dimethyl -2H-pyrano[3,2-c]pyridin-3-ol (E9)

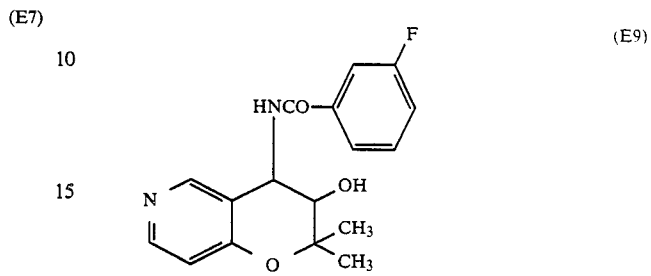
(E9)

The compound of this example was prepared in a similar manner, employing 3-fluorobenzoic acid, to that described in example 8. Recrystallisation from ethyl acetate-methanol gave the product of m.p. 259°–261° C. . Mass Spectrum (E.I.). M+ at m/z 316.1220. $C_{17}H_{17}N_2O_3F$ requires 316.1223.

EXAMPLE 10

Trans-4-(2,4-difluorobenzoylanino)-3,4-dihydro-2,2-dimethyl-2H-pyrano[3,2-c]pyridin-3-ol (E10)

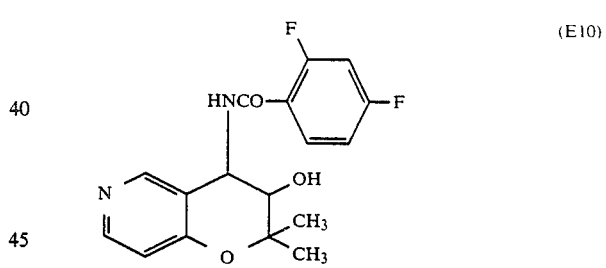
(E10)

The compound of this example was prepared in a similar manner, employing 2,4-difluorobenzoic acid, to the compound of example 8. Recrystallisation from ethyl acetate gave the compound of example 10 of m.p. 235°–237° C.

NMR (CD$_3$OD) δ 1.37 (s, 3H)

1.57 (s, 3H)

3.84 (d, J=10 Hz, 1H)

5.30 (d, J=10 Hz, 1H)

6.85 (d, J=6 Hz, 1H)

7.14 (irregular t, J=8 Hz, 2H)

7.87 (q, J=8 Hz, 1H)

8.23 (d, J=6 Hz, 1H)

8.36 (s, 1H)

EXAMPLE 11

Trans-4-(2,6-difluorobenzoylamino)-3,4-dihydro-2,2-dimethyl-2H-pyrano[3,2-c]pyridin-3-ol (E11)

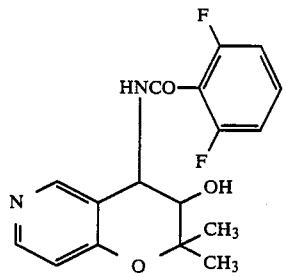

The compound of this example was prepared in a similar manner, employing 2,6-difluorobenzoic acid, to the compound of example 8. Recrystallisation from ethyl acetate-methanol furnished the compound of example 11 as a solid of m.p. 256° C.

Anal. Found: C,61.17; H,4.55; N,8.29%.

$C_{17}H_{16}N_2O_3F_2$ require: C,61.07; H,4.82; N,8.38%.

EXAMPLE 12

Trans-4-(N-acetyl-2-oxopiperazin-1-yl)-3,4-dihydro-2,2-dimethyl-2H-pyrano[3,2-c]pyridin-3-ol (E12)

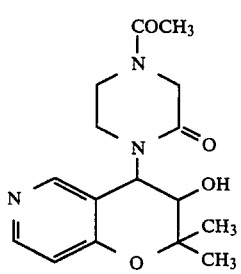

The epoxide (2.5 g, the preparation of which was described in example 1) and 4-acetylpiperazin-2-one (2.7 g) were stirred in dimethyl sulphoxide (30 mL). Sodium hydride (0.57 g, 80% dispersion in oil) was added in 5 portions to the solution at room temperature under nitrogen. The reaction mixture was stirred at room temperature for an additional 6 h. Water (25 mL) was added cautiously to the solution and the mixture extracted several times with chloroform. The organic extracts were washed with H2O and brine, and dried over anhydrous MgSO4. The solution was filtered and evaporated and the residual gum chromatographed on silica gel. Elution with 5% methanol-chloroform gave the product which was recrystallised from ethyl acetate-methanol to give the compound of example 12 (0.36 g) as a solid of m.p. 215°-217° C.

Anal. Found: C,60.24; H,6.59; N,13.16%.

$C_{16}H_{21}N_3O_4$ requires: C,60.18; H,6.63; N,13.16%.

EXAMPLE 13

Trans-4-(2-oxopiperazin-1-yl)-3,4-dihydro-2,2-dimethyl2H-pyrano[3,2-c]pyridin-3-ol (E13)

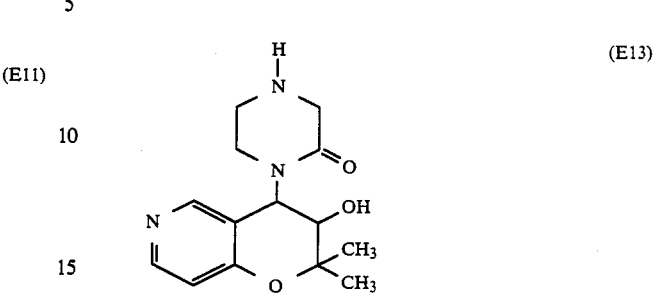

The compound of example 12 (0.64 g) was heated under reflux in 5N HCl (6 mL) and ethanol (10 mL) for 2 hours. The solution was cooled, partially evaporated and basified with KOH pellets. The mixture was evaporated to dryness, and taken up in hot ethyl acetate and filtered. Evaporation of solvent gave a residue which was recrystallised twice from ethyl acetate-methanol to give the compound of example 13 as a crystalline solid (156 mg) of m.p. 198°-199° C. Mass spectrum (E.I.) $(M+H)^+$ at m/z 278.1512. $C_{14}H_{20}O_3N_3$ requires 278.1504.

EXAMPLE 14

2,2-dimethyl-4-(2-oxopiperazin-1-yl)-2H-pyrano[3,2-c]pyridine (E14)

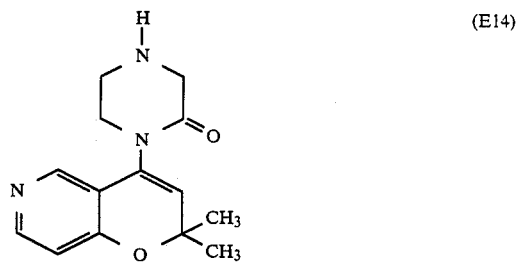

The compound of example 13 was treated in a similar manner to the compound of example 3 during the preparation of the compound of example 6, to furnish the title compound (E14) as a solid of m.p. 109°-110° C. after chromatography (chromatotron; elution with 15% methanol-chloroform).

PHARMACOLOGICAL DATA

Blood Pressure Lowering Activity

Systolic blood pressures were recorded by a modification of the tail cuff method described by I.M. Claxton, M.G. Palfreyman, R.H. Poyser, R.L. Whiting, European Journal of Pharmacology, 37, 179 (1976). A W+W BP recorder, model 8005 was used to display pulses. Prior to all measurements rats were placed in a heated environment (33.5±0.5° C.) before transfer to a restraining cage. Each determination of blood pressure was the mean of at least 6 readings. Spontaneously hypertensive rats (ages 12-18 weeks) with systolic blood pressures ≧180 mmHg were considered hypertensive.

| Compound of Example 1 | Time Post Dose Hrs | % Change in Systolic Blood Pressure |
|---|---|---|
| 6 Rats | 1 | −39 ± 7 |
| Dose 1 | | |
| mg/kg po | 2 | −29 ± 4 |
| Initial Blood | 4 | −17 ± 4 |
| Pressure | | |
| 238 ± 7 mmHg | 6 | −12 ± 4 |
| | 24 | −15 ± 3 |

The other compounds of the Examples were tested and found to be active in the above test.

Bronchodilator Activity—Guinea Pig Asphyxic Collapse Model in-vivo

This model is based on the method described by Herxheimer (Br.J.Pharm.50, 314 (1974)). Conscious guinea pigs (Dunkin-Hartley strain, 500-700 g body weight) were placed individually into a Perspex chamber of approximately 8 litres capacity, and the animals were challenged with an histamine aerosol. The standard histamine aerosol was generated using a Monaghan 675 ultrasonic nebulizer (power setting 7) from a $5 \times 10^{-6}$m solution of histamine diphosphate in distilled water. After obtaining satisfactory aerosol generation, the aerosol was passed into the chamber for 10 seconds and the time was recorded from introduction of the aerosol until the guinea pig collapsed (termed asphyxic collapse). In this way, the mean time to asphyxic collapse for a group of guinea pigs was determined.

Compounds were administered orally to groups of animals (number =N) and the degree of protection against histamine-induced asphyxic collapse was determined by the percentage increase in mean time to asphyxic collapse of a compound-treated group over that for asphyxic collapse for control groups. Compound-treated animals that did not collapse were considered to be 100% protected.

Compounds were administered in 1% methyl cellulose at a concentration of 5 mg/kg (1 ml/kg body weight) and the animals were challenged with the standard histamine aerosol after 30 min.

The significance of any increase in the mean asphyxic collapse time of a compound-treated group of animals over that of a vehicle-treated control group was determined using Student's "t" test.

The results were as follows:

| Compound | Dose (p.o.) | N | Mean Collapse time (sec) |
|---|---|---|---|
| example 3 | 5 mg/kg | 5 | 193.0 ± 7.0* |
| Control | | 5 | 67.8 ± 6.1 |

*p < 0.001 (Student's t-test).

We claim:

1. A compound of formula (I) or a pharmaceutically acceptable salt thereof:

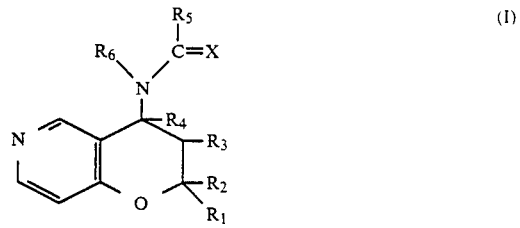

wherein one of $R_1$ and $R_2$ is hydrogen or $C_{1-4}$ alkyl and the other is $C_{1-4}$ alkyl or $R_1$ and $R_2$ together are $C_{2-5}$ polymethylene;

either $R_3$ is hydrogen, hydroxy, $C_{1-6}$ aklkoxy or $C_{1-7}$ acyloxy and $R_4$ is hydrogen or $R_3$ and $R_4$ together are a bond;

$R_5$ is hydrogen; $C_{1-6}$ alkyl optionally substituted by up to three halo atoms, by hydroxy, $C_{1-6}$ alkoxy, $C_{1-6}$ alkoxycarbonyl, carboxy; amino optionally substituted by one or two independent $C_{1-6}$ alkyl groups or pyrrolidinyl or piperidinyl; $C_{2-6}$ alkenyl; amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by one $C_{1-6}$ alkyl, $C_{1-6}$ alkoxy or halogen; or a member selected from the group consisting of phenyl, naphthyl, furyl, thienyl, pyrryl, oxazolyl, thiazolyl, imiazolyl, thiadiazolyl, pyridyl, pyridazyl pyrimidyl, pyrazyl, triazyl, benzofuranyl, benzothienyl, indolyl, indazolyl, quinolyl, isoquinolyl and quinazolyl, said member being optionally substituted by one to four groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups; or (when X is O), $R_5$ is selected from the class of carboxy, $C_{1-6}$ alkoxycarbonyl, or aminocarbonyl optionally substituted by one or two $C_{1-6}$ alkyl groups; and $R_6$ is hydrogen or $C_{1-6}$ alkyl; or $R_5$ and $R_6$ together are $-CH_2-(CH_2)_n-Z-(CH_2)_m-$ wherein m and n are to 2 such that m+n is 1 or 2 and Z is $CH_2$, 0, S or NR wherein R is hydrogen, $C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two of $C_{1-6}$ alkyl, $C_{1-6}$ alkoxy or halogen; or R is heteroarylcarbonyl wherein the heteroaryl moiety is a member selected from the group consisting of furyl, thienyl, pyrryl, oxazolyl, thiazolyl, imidazolyl, thiadiazolyl, pyridyl, pyridazyl, pyrimidyl, pyrazyl, triazyl, benzofuranyl, benzothienyl, indolyl, indazolyl, quinolyl, isoquinolyl and quinazolyl;

X is oxygen or sulphur; and the nitrogen containing group in the 4-position being trans to the $R_3$ group when $R_3$ is hydroxy, $C_{1-6}$ alkoxy or $C_{1-7}$ acyloxy.

2. A compound according to claim 1 wherein $R_1$ and $R_2$ are both methyl.

3. A compound according to claim 1, wherein $R_3$ is hydroxy and $R_4$ is hydrogen, or $R_3$ and $R_4$ together are a bond.

4. A compound according to claim 1, wherein the nitrogen atom at the 6- position of the pyranopyridine nucleus is in the form of an N-oxide.

5. A compound according to claim 1 wherein $R_5$ and $R_6$ are joined to form $-CH_2-(CH_2)_n-Z-(CH_2)_m-$ as defined in claim 1.

6. A compound according to claim 1 wherein $R_5$ is methyl or $R_5$ is phenyl or amino either being optionally substituted as defined in claim 1; and $R_6$ is methyl, ethyl or hydrogen.

7. A compound selected from the group consisting of:
trans-3,4-dihydro-2,2-dimethyl-4-(2-oxopyrrolidin-1-yl) -2H-pyrano[3,2-c]pyridin-3-ol,
trans-3,4-dihydro-2,2-dimethyl-4-(2-oxopiperidin-1-yl)-2H-pyrano[3,2-c]pyridin-3-ol,
trans-4-acetylamino-3,4-dihydro-2,2-dimethyl-2H-pyrano[3,2-c]pyridin-3-ol,
trans-4-(4-fluorobenzoylamino)-3,4-dihydro-2,2-3 dimethyl-2H-pyrano[3,2-c]pyridin-3-ol,
2,2-dimethyl-4-(2-oxopiperidin-1-yl)-2H-pyrano[3,2-c]pyridine,
trans-4-(2-fluorobenzoylamino)-3,4-dihydro-2,2-dimethyl-2H-pyrano[3,2-c]pyridin-3-ol,
trans-4-(3-fluorobenzoylamino)-3,4-dihydro-2,2-dimethyl-2H-pyrano[3,2-c]pyridin-3-ol,
trans-4-(2,4-difluorobenzoylamino)-3,4-dihydro-2,2-dimethyl-2H-pyrano[3,2-c]pyridin-3-ol,
trans-4-(2,6-difluorobenzoylamino)-3,4-dihydro-2,2-dimethyl-2H-pyrano pyridin-3-ol,
trans-4-(N-acetyl-2-oxopiperazin-1-yl)-3,4-dihydro-2,2-dimethyl-2H-pyrano pyridin -3-ol,
trans-4-(2-oxopiperazin-1-yl)-3,4-dihydro-2,2-dimethyl-2H-pyrano pyridin -3-ol, and
2,2-dimethyl-4-(2-oxopiperazin-1-yl)-2H-pyrano-[3,2-c]pyridin-3-ol, and pharmaceutically acceptable salts of any of the foregoing.

8. An antihypertensive pharmaceutical composition comprising an effective amount of a compound according to claim 1 or a pharmaceutically acceptable salt thereof, and a pharmaeutically acceptable carrier.

9. A method of treatment of hypertension in mammels, which comprises administering to the mammal an antihypertensive effective amount of a compound according to claim 1 or a pharmaceutically acceptable salt thereof.

* * * * *